United States Patent [19]
Klupt

[11] Patent Number: 5,301,381
[45] Date of Patent: Apr. 12, 1994

[54] TOOTHBRUSH SYSTEM

[76] Inventor: Michael F. Klupt, 7 Thistledell Ct., Owings Mills, Md. 21117

[21] Appl. No.: 986,560

[22] Filed: Dec. 7, 1992

[51] Int. Cl.⁵ .................... A61C 17/34; A46B 13/04
[52] U.S. Cl. ........................................ 15/22.1; 15/29
[58] Field of Search ............... 15/22.1, 22.2, 28, 29; 433/216

[56] References Cited

U.S. PATENT DOCUMENTS

| | | |
|---|---|---|
| 1,981,688 | 11/1934 | Conti . |
| 2,140,307 | 12/1938 | Belaschk et al. . |
| 2,184,212 | 12/1939 | Davidson . |
| 2,215,031 | 9/1940 | Elmore . |
| 2,226,145 | 12/1940 | Smith . |
| 2,285,505 | 6/1942 | Grout et al. . |
| 2,317,314 | 4/1943 | Van Haaften . |
| 2,546,754 | 3/1951 | Jones . |
| 2,841,806 | 7/1958 | Blasi . |
| 3,022,789 | 2/1962 | Rallis et al. . |
| 3,039,123 | 6/1962 | Brucker et al. . |
| 3,056,151 | 10/1962 | Vlacancich . |
| 3,195,537 | 7/1965 | Blasi . |
| 3,242,516 | 3/1966 | Cantor . |
| 3,261,367 | 7/1966 | Pickering . |
| 3,549,268 | 12/1970 | Casselman . |
| 3,825,354 | 7/1974 | Rallis . |
| 3,869,746 | 3/1975 | Man-king . |
| 3,892,237 | 7/1975 | Steiner . |
| 3,977,084 | 8/1976 | Sloan . |
| 4,079,517 | 3/1978 | Zacharia . |
| 4,274,173 | 6/1981 | Cohen . |
| 4,296,071 | 10/1981 | Weiss et al. . |
| 4,332,497 | 6/1982 | Rodriguez . |
| 4,467,822 | 8/1984 | Blackwell . |
| 4,583,563 | 4/1986 | Turner . |
| 4,619,009 | 10/1986 | Rosenstatter ............... 15/29 |
| 4,759,383 | 7/1988 | Phillips . |
| 4,827,552 | 5/1989 | Bojar et al. ............... 15/28 |
| 4,845,795 | 7/1989 | Crawford et al. ........... 15/22.1 |
| 4,950,247 | 8/1990 | Rosenblatt . |
| 4,955,567 | 9/1990 | Longhurst . |
| 4,963,046 | 10/1990 | Eguchi . |
| 5,142,723 | 9/1992 | Lustig et al. ............. 15/22.1 |

FOREIGN PATENT DOCUMENTS

| | | |
|---|---|---|
| 2019003 | 11/1971 | Fed. Rep. of Germany . |
| 3544256 | 6/1987 | Fed. Rep. of Germany ....... 15/22.1 |

OTHER PUBLICATIONS

PCT Publication WO 81/02247.
PCT Publication WO 84/02453.

Primary Examiner—Edward L. Roberts
Attorney, Agent, or Firm—Morton J. Rosenberg; David I. Klein

[57] ABSTRACT

A toothbrush system is provided which includes a handle member (14) which defines an internal handle chamber (22) for containment therein of a cleansing liquid container (28). The handle member (14) is coupled to a head housing (24) which has bristles (20) extending from it. The bristles (20) are displaceably oscillated about a central axis (16) and simultaneously are rotated about an axis which extends in a perpendicular direction to the longitudinal direction (18) and is responsive to the oscillating displacement of the bristles (20). A mechanism is provided for delivering a liquid from the handle (14) through the head member (12) and external the toothbrush system adjacent the bristles (20). In this manner, there is provided pulsating liquid flow from the toothbrush system with a combined rotation and oscillation of the toothbrush bristles (20) in a plurality of planes.

18 Claims, 6 Drawing Sheets

TOOTHBRUSH SYSTEM

BACKGROUND OF THE INVENTION

1. Field of the Invention

This invention pertains to a portable toothbrush system which is adapted to contain and apply all of the necessary brushing motions and application of cleansing fluids which may include astringent, fluoride, tartar control, antimicrobial, and/or whitening agents as well as prescription or over the counter medications, during normal operational modes when the user is brushing his or her teeth. Additionally, in further overall concept, this invention is directed to a portable toothbrush system which may be easily loaded with cleansing fluid agents as previously described from a reservoir and then removed for the brushing operation. In particular, the invention relates to a portable toothbrush system which has low maintenance and contains cleansing liquid with a further advantage of such liquid being applied to the teeth being brushed in a pulsating flow while the bristles of the toothbrush are displaced in a plurality of planes in order to enhance penetration of fluids into dental sulci and interdental spaces. Further, in general concept, this invention describes a portable toothbrush system which has the advantages of fluid injection units, and rotating as well as reciprocating bristles, wherein all of the necessary motions are combined into one overall system for maximizing the effects of the toothbrushing operation. Further, the subject system has as its overall concept to provide a total toothbrushing and irrigating system which will not require behavior modification by the user. In essence, the subject concept directs itself to a system which minimizes any interface with the user with the exception of the brushing operation. Further, the subject invention concept relates to a toothbrush system which may easily be manipulated in one hand of a user during the brushing operation to allow for ease of use devoid of connecting tubes or wires.

In particular, this invention relates to a toothbrush system having a handle member which has an internal chamber containing a liquid container for dispensing pulsating cleaning liquid adjacent and through the bristle tufts of a toothbrush during a toothbrushing operation. Still further, this invention pertains to a toothbrush system which includes a mechanism for actuating and causing a pulsating cleaning liquid flow from a liquid container located in the handle through the bristles for impingement onto the teeth or gum tissue of the user during the brushing operation. Still further, this invention relates to a toothbrush system which includes a cleansing liquid container which may easily be filled after dispensation of the cleaning fluid from the liquid container. Still further, this invention describes a portable toothbrush system which may be inserted onto a toothbrush stand having a reservoir of cleansing fluid wherein a stand conduit is insertable within the liquid container located within the handle section of the toothbrush system.

More in particular, this invention directs itself to a toothbrush system where a plurality or multiplicity of reservoirs may be mounted on a stand conduit and automatically allows cleansing liquid to fill the liquid container within the handle section of the toothbrush system.

Still further, this invention relates to a toothbrush system where the bristles mounted on a head of the toothbrush are rotated in a plurality of planes simultaneously. Still further, this invention describes a system for an oscillating arcuate displacement of the bristles of the toothbrush about a central axis of the toothbrush. Further, this invention relates to a toothbrush system which allows for rotative actuation of the toothbrush bristles about an axis which is normal to the central axis of the handle member of the toothbrush. Additionally, this invention describes a mechanism for combining simultaneously the oscillating arcuate displacement of the bristles about the central axis of the toothbrush as well as for the rotative actuation of the toothbrush bristles about an axis normal to the central axis of the toothbrush. Further, this invention directs itself to a portable toothbrush system which simultaneously and concurrently provides for a pulsating cleansing liquid flow to pass adjacent the bristles of the toothbrush while providing rotation of the bristles in a plurality of planes during the toothbrushing operation.

Of further importance is that the subject toothbrush system pertains to a system where the toothbrush head is maintained as a stationary unit while the toothbrush bristles are actuated into a reciprocating arcuate path when operational in the mouth of a user.

2. Prior Art

Toothbrush systems which allow for the rotation of the toothbrush bristles are known in the art. The best prior art known to Applicant includes U.S. Pat. Nos. 4,963,046; 3,022,789; 3,825,354; 3,261,367; 4,332,497; 4,955,567; 4,759,383; 4,296,071; 3,549,268; 4,467,822; 4,583,563; 2,184,212; 4,950,247; 2,546,754; and, 3,892,237.

In some prior art systems such as that shown in U.S. Pat. No. 4,963,046, there are cartridge-type storage portions which are removably connected to the toothbrush system. Additionally, such prior art systems show communication passages for supplying the oral use fluid from the storage to the bristle implanted surface on the brush base. However, such prior art systems do not provide for the pulsating type of cleansing liquid flow which is advantageous to the removal of contaminants within the mouth of a user. Additionally, such prior art systems do not show the simultaneous pulsating fluid flow in combination with the multiplicity of rotational planes for the bristles during use.

Other prior art systems such as that shown in U.S. Pat. No. 3,022,789 provide for injector-type toothbrushes for receiving toothpaste from a high pressure system such as an aerosol bomb. Such do provide for a hollow type toothbrush with a detachable injector however, such do not provide for the combination of bristle rotations in a plurality of planes with the pulsating fluid flow of the subject system.

Other prior art such as that shown in U.S. Pat. No. 3,825,354 describe toothbrush adaptors for aerosol containers however, such do not provide for the advantageous pulsating fluid flow as is necessary to the subject system.

Basically, there are prior art systems which include rotating heads as bristles which are advantageous for application to specific gum or tooth areas and include heads that oscillate through an approximate 90° angle. However, although sufficient for cleaning generally flat surfaces, such prior art is disadvantageous for arcuate surfaces of teeth and cannot clean well between a user's teeth.

Other prior art systems include rotating bristles which are advantageous for application between teeth, but are not efficient for cleaning flat areas, and in some cases may be abrasive to gum tissue.

Such prior art systems do not provide for the advantageous bristle rotation and oscillatory displacement in separate planes simultaneously while providing a stream and spray of cleansing liquid to remove contaminants wherein the overall system is self-refilling, wireless and tubeless.

Additionally, prior art systems do not provide for a stationary head housing allowing the bristles to be reciprocally and reversibly displaced which provides the user additional comfort during the brushing operation.

SUMMARY OF THE INVENTION

There is provided a toothbrush system which includes a handle member defining an internal handle chamber. The handle member extends in a longitudinal direction and is coupled to a longitudinally extended head member defining a head housing having bristles extending therethrough. A mechanism is provided for displaceably oscillating the bristles with respect to the head housing about a central axis of the head member and the handle member defined by the longitudinal direction. A mechanism is further provided for rotating the bristles about an axis extending normal to the longitudinal direction responsive to the displaceable oscillation of the bristles. A liquid delivery system is provided to deliver the liquid from the handle member through an interior of the head member and then through the head housing adjacent the bristles. A power drive mechanism is provided which includes a motor mounted within the internal handle chamber for displaceably oscillating the bristles, rotating the bristles and delivering the liquid external the head housing.

A primary object of the present invention is to provide a portable toothbrush system which requires a minimal amount of maintenance by the user.

A further primary object of the instant invention is to provide a toothbrush system which does not require behavior modification and allows the user to continue his or her normal brushing habits while maximizing the effect through rotation of the toothbrush bristles in a plurality of planes and use of a pulsating cleansing liquid.

Another object of the subject invention is to provide a singular toothbrush system which replaces a plurality of toothbrush and irrigation devices and may be used by the user in a normal toothbrush operation without any change of the behavior of the user being necessitated.

DESCRIPTION OF THE PREFERRED EMBODIMENTS

Referring now to FIGS. 1–8, there is shown toothbrush system 10 for optimizing removal of contaminants from the teeth and gums of a user. As will be described in following paragraphs, system 10 provides the user with the maximization of bristle-tooth interface while simultaneously providing a fluid force to remove unwanted contaminants. Additionally, system 10 provides the user with a completely portable system devoid of hook-up tubes and connectors.

In particular, toothbrush system 10 provides for a multiplicity of rotational and oscillatory displacements of bristles 20 to be further described in following paragraphs. Additionally, and simultaneous to the plurality of displacements of bristles 20, there is provided mechanisms whereby a cleansing liquid is actuated to provide a pulsating flow through and adjacent bristles 20 which are being displaced in a plurality of planes. In this manner, contaminants are effectively removed from the surface of the teeth by the combined brushing action and removed by the liquid spray and flow.

It is to be understood that the term cleansing liquid hereinafter referred to in following paragraphs may refer to general types of cleansing liquids such as plaque fighting liquids, dentifrice type liquids, or simply salt water solutions, not important to the inventive concept as is herein described.

Figure 1:
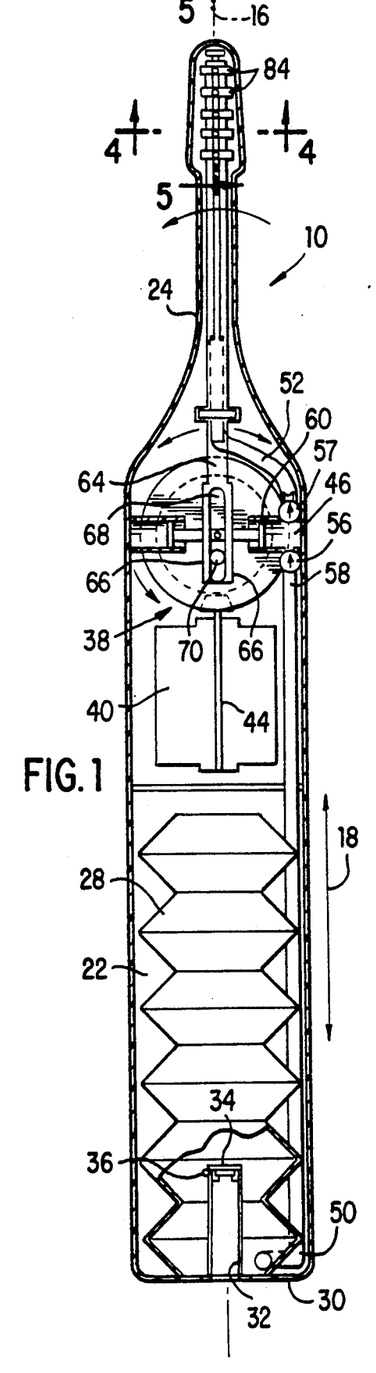
FIG. 1 is a front elevational cross-sectional view of the toothbrush system.
Figure 2:
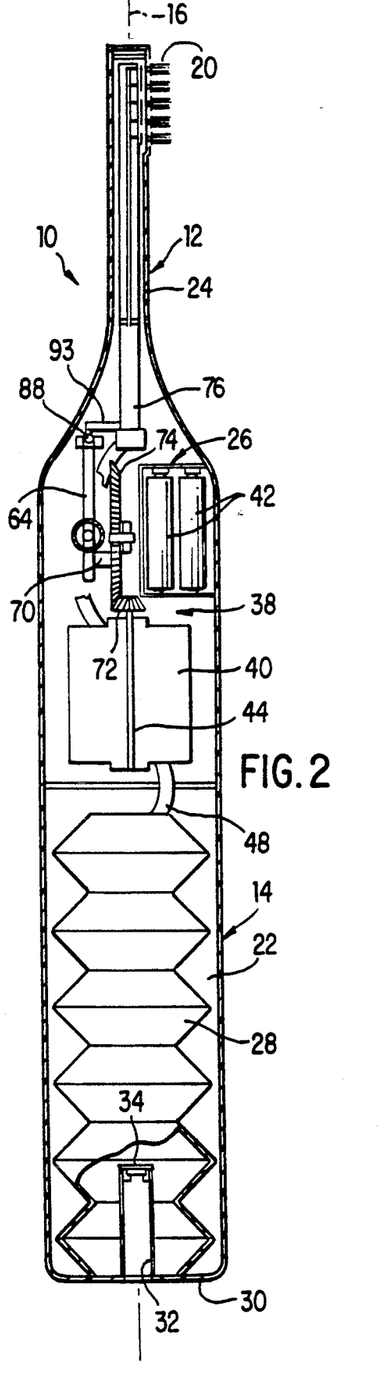
FIG. 2 is a side elevational cross-sectional view of the toothbrush system.
Figure 4:
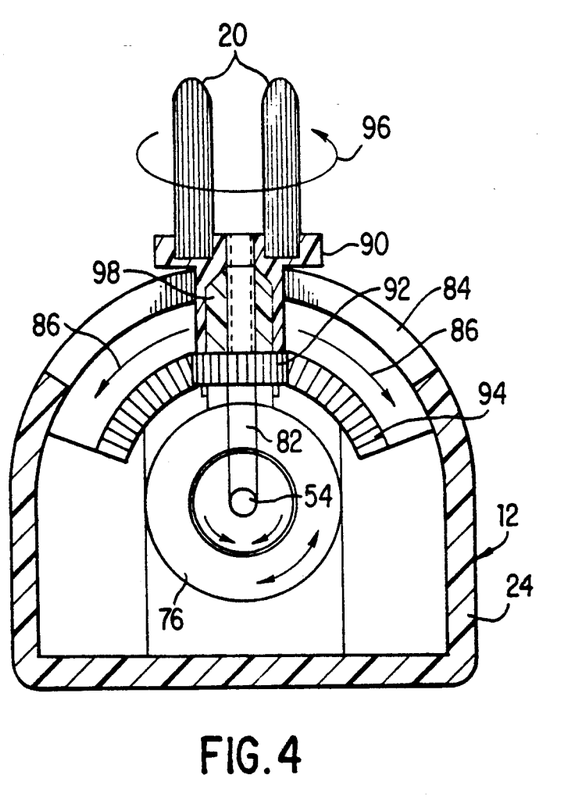
FIG. 4 is a cross-sectional view of the head member of the toothbrush system.

Referring to FIGS. 1, 2 and 4, there is seen that toothbrush system 10 includes handle member 14 having internal handle chamber 22. As can be seen, handle member 14 extends in longitudinal direction 18 as defined by the directional arrow shown in FIGS. 1 and 2. Handle member 14 may be formed of one-piece or multi-piece molded plastic or some like material not important to the inventive concept as herein described with the exception that it have a diameter which allows a user to easily hold toothbrush system 10 in one hand during a normal brushing operation.

Handle member 14 may include a standard commercially available on/off switch (not shown) for activating motor 40 responsive to electrical input from standard batteries 42 and may further include a push button valve to control fluid flow. Such electrical switches and valves are well known in the prior art and are not part of the invention concept as herein described.

Figure 5:
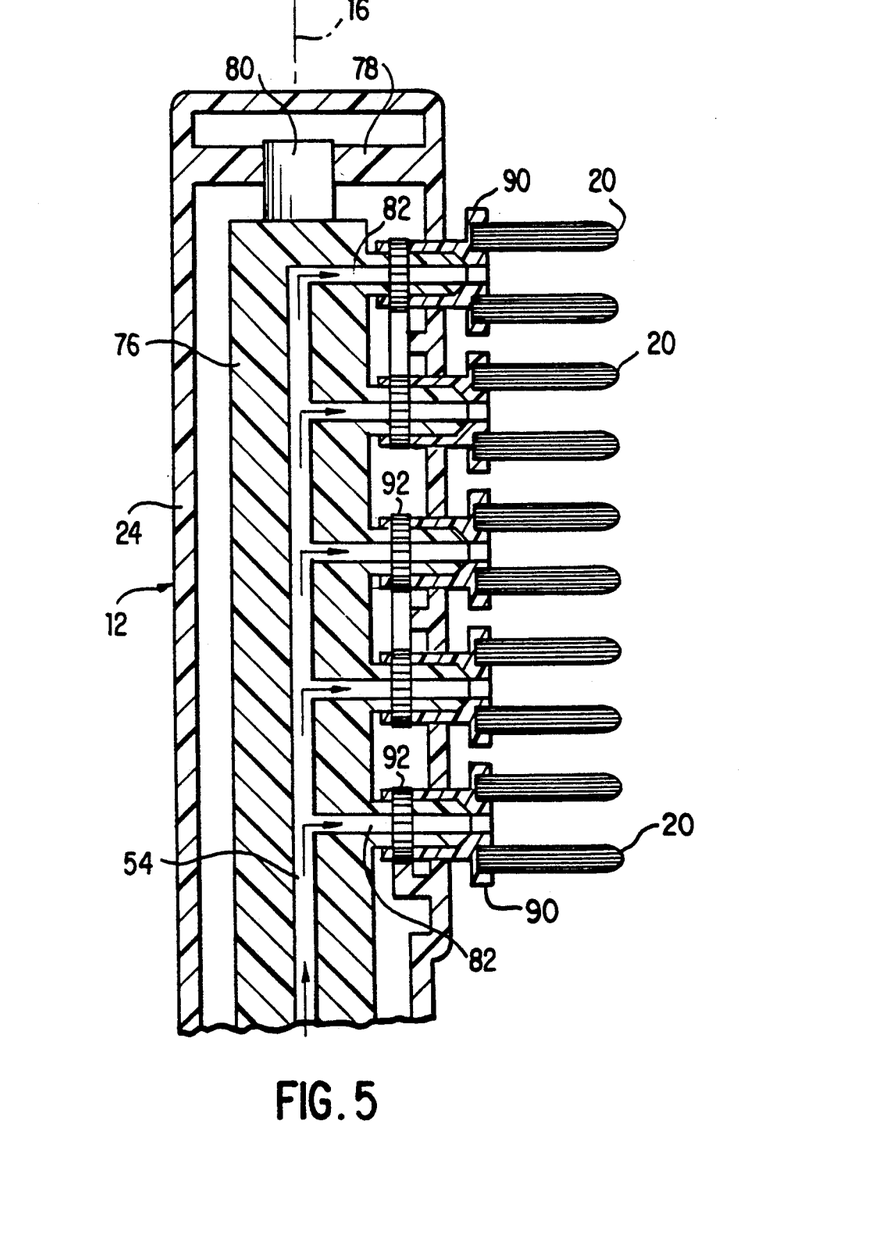
FIG. 5 is a partially cutaway cross-sectional view of the head member showing fluid passageways.

Head member 12 also extends in longitudinal direction 18 and defines head housing 24 and includes sets of bristles 20 extending external head housing 24, more clearly seen in FIGS. 2, 4 and 5. Head member 12 and associated housing 24 may be integrally molded or may be releasably secured to handle member 14 through a standard keyway interface not important to the invention concept as herein described with the exception that head housing 24 be removable from handle member 14. Head housing 24 in a manner similar to handle member 14 may be formed of a plastic type composition and may be molded in one or multi-piece formation.

Figure 6:
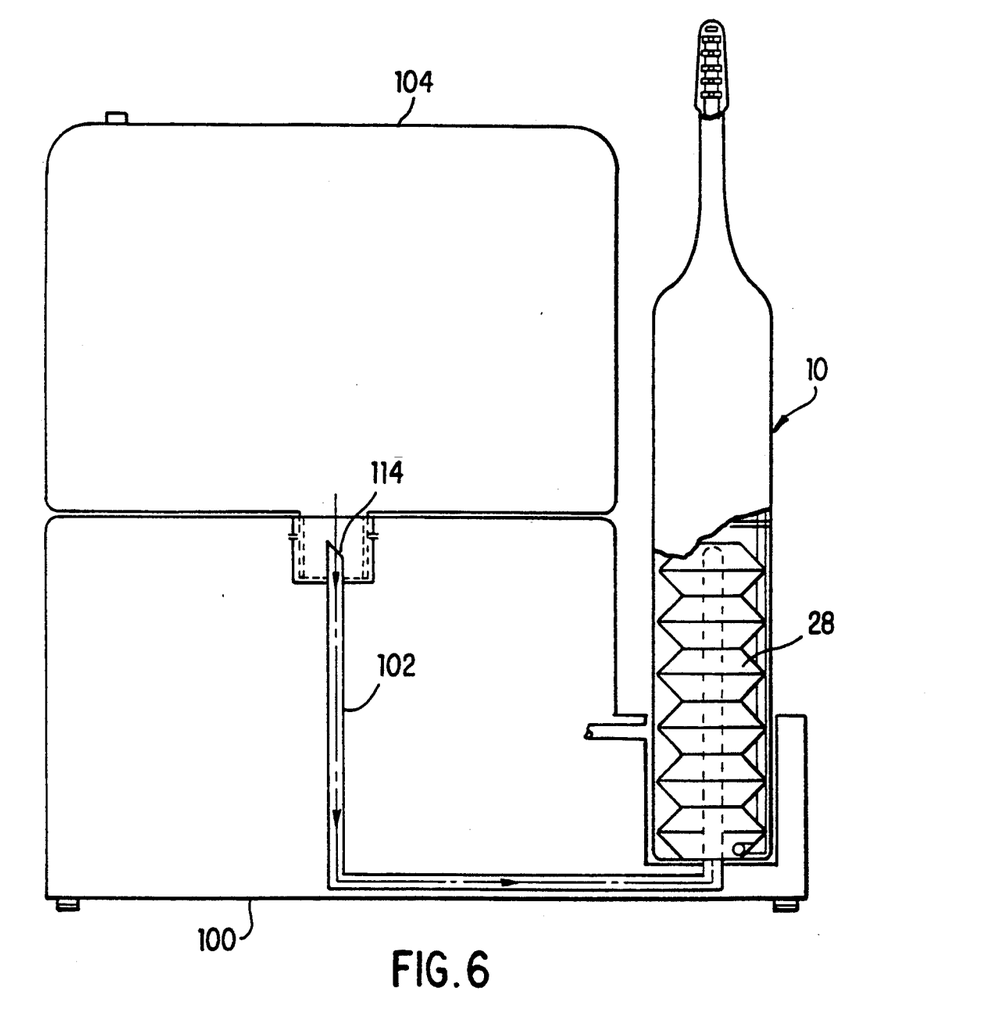
FIG. 6 is a partially cutaway elevational view of the toothbrush system mounted in fluid communication with a cleansing liquid reservoir.
Figure 7:
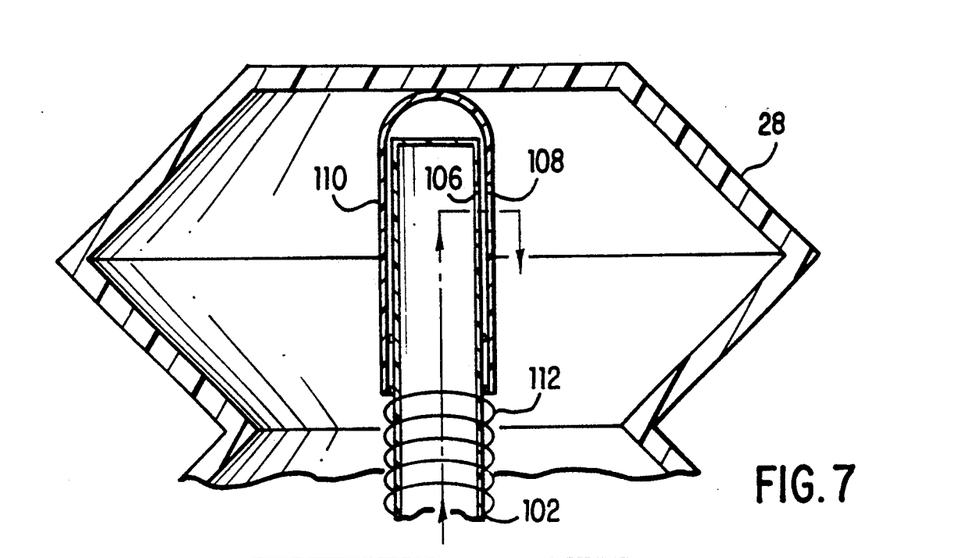
FIG. 7 is a cross-sectional partially cutaway view of a liquid container having cleansing liquid inserted therein through a stand conduit; and, FIG. 8 is an elevational partially cutaway view of the liquid container wherein the stand conduit is being removed and liquid flow is terminated.
Figure 8:
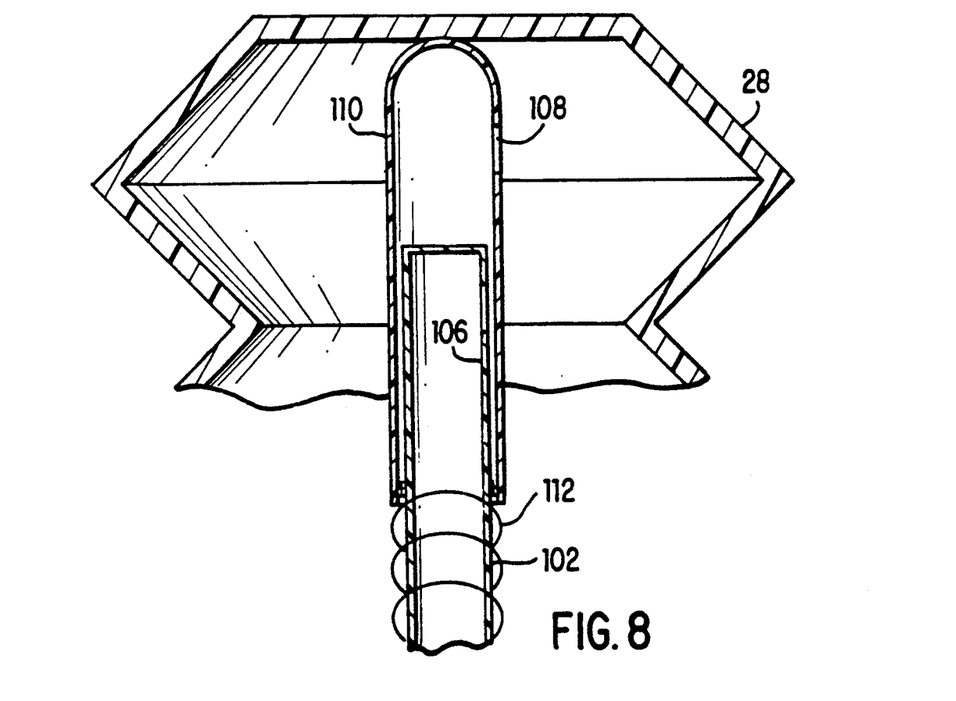

Toothbrush system 10 includes liquid container 28 shown in FIGS. 1, 2 and 6 as well as partially shown in FIGS. 7 and 8 to provide a dispensing container for the cleansing liquid. Liquid container 28 is mounted within internal handle chamber 22 for dispensing the liquid responsive to a pressure differential created when the toothbrush system is actuated. Liquid container 28 is formed of a flexible bellows type contour and is in fluid communication with head member 12 as will be further described in following paragraphs. Bellows type liquid container 28 may be formed of a flexible material such as a plastic composition or some like composition which is inert to the cleansing liquid contained therein. Bellows container 28 is collapsible as cleansing liquid is dispensed therefrom and may be expanded when filled with cleansing liquid as will be described in following paragraphs when taken with relation to FIGS. 6-8.

Bellows container 28 is secured to bottom wall 30 of handle member 14. As can be seen in FIGS. 1 and 2, liquid container 28 includes container conduit 32 formed through bottom wall 30 of handle member 14 and further includes trap door member 34 which is rotatable with respect to container conduit 32 through container hinge 36. Hinge 36 may be a standard spring hinge which is biased in a manner to block or close the container conduit passageway during use but may cause opening of trap door 34 upon application of pressure. Other types of self sealing devices may be used and the inventive concept is not limited to the description herein described. In this manner, and as will be more fully described in following paragraphs, cleansing liquid may be inserted through container conduit 32 to the internal portion of liquid container 28 to fill liquid container 28. However, trap door member 34 does not allow egress of cleansing liquid contained in liquid container 28 since it maintains a closed state when toothbrush system 10 is in operation.

Toothbrush system 10 further includes drive mechanism 38 seen in FIGS. 1 and 2 which allows for the portability of toothbrush system 10 while maintaining a high torque actuation and displacement operation. Drive mechanism 38 is mounted within internal handle chamber 22 for displaceably oscillating bristles 20 while simultaneously allowing rotation of bristles 20 and further delivering the cleansing liquid external head housing 24. Drive mechanism 38 includes a standard DC high torque motor 40 which is commercially available and utilized commercially in a number of portable toothbrush systems. Additionally, drive mechanism 38 includes standard batteries 42 which may be rechargeable for providing electrical energy to drive motor 40 and corresponding motor shaft 44. For ease of replaceability for the user, batteries 42 may be provided in a battery pack housing 26, insertable into chamber 22 in total without the necessity of the user changing individual batteries 42.

Figure 3:
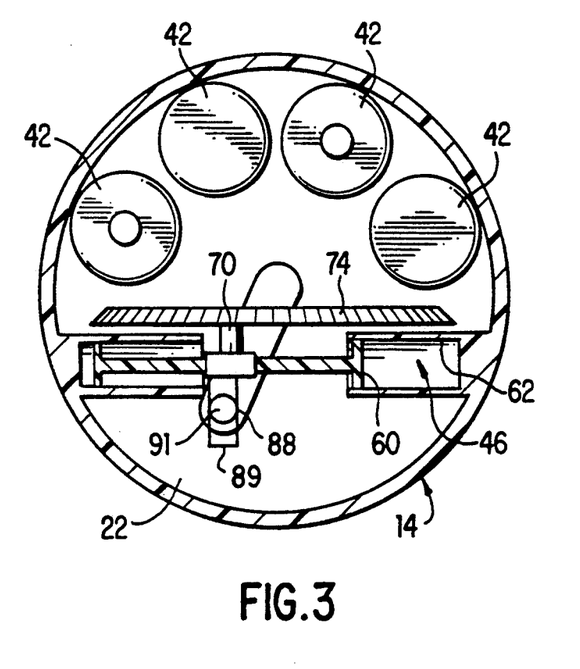
FIG. 3 is a cross-sectional view of the toothbrush system taken along a central axis line.

Toothbrush system 10 includes liquid delivery mechanism 46 clearly seen in FIG. 1 and FIG. 3. Liquid delivery mechanism 46 includes first liquid conduit 48 shown in FIGS. 1 and 2 which is in fluid communication with liquid container 28 at first liquid conduit first end 50. Additionally, liquid delivery mechanism 46 further includes second liquid conduit 52 which is in fluid communication with head flow passageway 54 seen in FIGS. 4 and 5. Standard one-way valve 56 is mounted on first liquid conduit second end 58 as is seen in FIG. 1. In this manner, cleansing liquid may be dispensed from liquid container 28 through first liquid conduit 48 and then through one-way valve member 56. One-way valve member 56 ensures that cleansing liquid will not be passed in a reverse manner into first liquid conduit 48.

Liquid delivery mechanism 46 further includes a mechanism for actuating one-way valve member 56. As is seen in FIGS. 1 and 3, there is provided linearly and reversibly displaceable piston member 60 which is coupled to the overall drive mechanism 38 and is displaceable within piston chamber 62. As is seen, piston chamber 62 is in fluid communication with second liquid conduit 52 and one-way valve member 56 on opposing longitudinal ends as is seen in FIG. 1. Additionally, drive mechanism 38 creates a pressure differential between the piston chamber 62 and first liquid conduit 48 to allow liquid to flow from first liquid conduit 48 into piston chamber 62 and then consequently into second liquid conduit 52 for dispensation through head flow passageway 54. As can be seen in FIG. 3, as piston member 60 moves in a radial direction toward an outer wall of handle member 14 within internal handle chamber 22, liquid contained within piston chamber 62 is forced into second liquid conduit 52 but is blocked from passage into first liquid conduit 48 by one-way valve member 56.

Also included, as shown in FIG. 1, is secondary one-way valve 57 which is mounted at the entrance of secondary conduit 52 to prevent backflow of fluids and air into piston chamber 62. Thus when a low pressure is provided in chamber 62, fluids will not pass thereto from conduit 52.

As piston member 60 is linearly displaced within piston chamber 62 in a direction toward central axis 16, a lower pressure is obtained within piston chamber 62 which closes valve 57 and opens one-way valve member 56 and allows cleansing fluid to be dispensed therein.

As piston chamber 60 reversibly moves in a linear direction within piston chamber 62, a pulsating liquid flow is provided through second liquid conduit 52. As piston 60 moves radially outward, the fluid within chamber 60 is compressed and a resulting higher pressure ensues. Fluid is then passed into second conduit 52 and not into first liquid conduit 48 due to the action of one-way valve 56. This pulsating flow of cleaning liquid eventually egresses between sets of bristles 20 for optimizing the removal of contaminants in the user's mouth.

As has been seen and described, piston member 60 is reversibly moved in a linear direction. Toothbrush system 10 further includes a mechanism for converting the rotational displacement of drive mechanism 38 to the linear and reversible displacement provided to piston member 60. The mechanism for converting the rotational displacement of drive mechanism 38 includes longitudinally extending fork member 64 which includes opposing fork member sidewalls 66 defining longitudinally directed fork slot 68. Fork pin member 70 is slidable within fork slot 68 as is seen in FIGS. 1 and 2. Fork pin member 70 is displaceable within fork slot 68 responsive to actuation by drive mechanism 38. Toothbrush system 10 includes a mechanism for displacing fork pin member 70 and having first bevel gear 72 mounted on longitudinally extending motor shaft 44 as is seen in FIG. 2. Second bevel gear 74 is matingly engaged with first bevel gear 72 for rotation of second bevel gear 74 about a second bevel gear axis which extends normal to longitudinal direction 18. As is seen, fork pin member 70 is secured to an outer surface of second bevel gear 74 and extends in a direction substantially parallel to the axis of the second bevel gear 74.

Piston member 60 is fixedly secured or molded in one-piece formation to one of opposing fork sidewalls 66 and extends transverse thereto for linear reversible displacement into piston chamber 62 as has previously been described. Displacement of piston member 60 is responsive to a displacement of fork pin member 70. Thus, as motor shaft 44 is rotatably driven by motor 40, first bevel gear 72 is provided with a rotational displacement about central axis 16 of toothbrush system 10. First bevel gear 72 matingly engages second bevel gear 74 which is a right-angle coupling and results in second bevel gear 74 being rotated about an axis substantially normal to central axis 16. Fork pin member 70 is mounted off-center to second bevel gear 74 and as second bevel gear 74 rotates, fork pin member 70 slidably engages fork slot 68 which responsively drives piston member 60 in a linear and reversible manner as second bevel gear 74 rotates.

In this manner, a pulsating flow of cleansing liquid passes from the internal portion of liquid container 28 through first liquid conduit 48, one-way valve 56, valve 57, and into second liquid conduit 52.

Referring now to FIGS. 4 and 5, there is shown head member 12 and associated head housing 24. In particular, referring to FIG. 5, there is shown head flow passageway 54 which is in fluid communication with second liquid conduit 52 as has hereinbefore been described. Head shaft member 76 is rotatably mounted in head wall 78 through bearing shaft 80 as is seen in FIG. 5. In this manner, head shaft member 76 may rotate about central axis 16. Additionally, flow of pulsating liquid passes through head flow passageway 54 and communicates with branch conduits 82 as is shown in FIGS. 5 and 4.

As can be seen in FIG. 4, head slots 84 are formed through head housing 24 on an upper portion thereof to allow extension therethrough of bristles 20. A plurality of head slots 84 are provided as is shown in FIG. 1. In this manner, as will be seen in following paragraphs, bristles 20 are then free to be driven in an oscillating rotative direction as shown by the directional arrows 86 in FIG. 4 responsive to the concatenation of elements to be further described.

The mechanism for displaceably oscillating bristles 20 in arcuate direction 86 includes the extended head shaft member 76 being coupled to longitudinally directed fork member 64 through ball-slider joint 88 shown in FIG. 2. Referring to FIG. 3, as piston member 60 is linearly displaced, raceway member 89 is responsively linearly displaced. Ball member 91 rides within raceway member 89 to cause oscillation of lug member 93 and responsive oscillation of head shaft member 76. Head shaft member 76 is journaled in head housing 24 which remains stationary as bristles 20 are oscillated. This combination of elements provides for the conversion of the displacement of fork member 64 to an oscillating rotative displacement of longitudinally directed head shaft member 76 about central axis 16. This has the resultant effect of providing the oscillating rotative displacement of bristles 20 within respective slots 84. As can be seen, as pin member 70 is rotated through the corresponding rotation of second bevel gear 74, fork member 64 rotates with respect to head shaft member 76 through ball joint 88 and correspondingly displaces head shaft member 76 in the rotative displacement about central axis 16.

Referring now to FIGS. 4 and 5 once again, there is provided a mechanism for rotating bristles about an axis substantially normal to longitudinal direction 18 and central axis 16. Bristle head members 90 extend radially through slots 84 as is seen in FIG. 4. Bristles 20 are fixedly secured to bristle head members 90 through molding or some like technique not important to the inventive concept as herein described. Bristle head members 90 are rigidly coupled on a lower end thereof to bristle pinion gears 92 which matingly engage stationary rack gears 94. It is to be understood, that a single stationary rack gear may be used in combination with mating pinion gears 92 which drive each other. Bristle head members 90 and corresponding bristle pinion gears 92 are rotatable in the direction defined by directional arrow 96 through bearing core 98. Thus, bristle head members 90 are rotatable in direction 96 with respect to stationary head member 12 when oscillation occurs in the arcuate direction 86.

In this manner, when head shaft member 76 is rotated in the direction of arrows 86, bristle head pinion gears 92 matingly engage with rack gears 94. Bristle head members 90 are rotatable on bearing core 98 to allow for rotation of bristles 20 in arcuate direction 96. Thus, a simultaneous movement of bristles 20 is provided through use of toothbrush system 10 which allows for bristles 20 to be rotated in direction 96 while at the same time oscillating in arcuate direction 86.

Further, and simultaneous with the multiplicity of displacements of bristles 20, pulsating fluid passes through head flow passageway 54 from second liquid conduit 52 and enters branch conduits 82 formed through bristle head members 90 as is seen. Pulsating cleansing liquid is then egressed from head housing 24 external toothbrush system 10.

Referring now to FIGS. 6–8, there is shown toothbrush stand 100 adapted for filling liquid container 28 with cleansing liquid. Toothbrush stand 100 may be mounted on a base surface or wall mounted and includes stand conduit 102 for insert into reservoir 104 which contains the cleansing liquid. Stand conduit 102 is generally U-shaped in contour and is inserted within liquid container 28 through container conduit 32 as provided in FIG. 1. Stand conduit 102 has opening 106 formed in a sidewall thereof which is alignable with opening 108 formed through sheath member 110 as shown in FIG. 7. Spring member 112 bears against sheath 110 to maintain conduit opening 106 and sheath opening 108 out of alignment as is shown in FIG. 8. When liquid container 28 is to be filled, toothbrush system 10 is inserted over stand conduit 102 which is forced against an upper wall of liquid container 28 as shown in FIG. 7. In this condition, openings 106 and 108 are aligned and fluid passes from reservoir 104 through conduit 102 and then respectively through openings 106 and 108 into the interior of liquid container 28 to provide filling of liquid container 28 with cleansing fluid. When the filling process has been completed, toothbrush system 10 is removed from stand conduit and as is seen in FIG. 8. Openings 106 and 108 are misaligned and no fluid from reservoir 104 passes into liquid container 28. Additionally, reverse fluid flow is also terminated.

As is seen in FIG. 6, conduit 102 may include a sharpened end 114 which is insertable into a lip section of reservoir 104. Reservoir 104 is removable from toothbrush stand 100 and may be replaced with another reservoir 104.

In this manner, there has now been provided a portable toothbrush system 10 which provides the user with an optimized type of brushing action. Additionally, toothbrush system 10 allows for an internal liquid container to be filled at the discretion of the user and allows simple removal therefrom.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended Claims.

What is claimed is:

1. A toothbrush system comprising:
   (a) a handle member defining an internal handle chamber containing a liquid, said handle member extending in a longitudinal direction;
   (b) a longitudinally extended head member defining a stationary head housing having bristles extending therethrough;
   (c) means for displaceably oscillating said bristles with respect to said stationary head housing about a central axis of said head member and said handle member defined by said longitudinal direction;
   (d) means for rotating said bristles about an axis extending normal said longitudinal direction responsive to said displaceable oscillation of said bristles; and,
   (e) means for delivering said liquid contained in said handle member from said handle member through an interior of said head member and through said head housing adjacent said bristles, said means for displaceably oscillating said bristles, said means for rotating said bristles, and said means for delivering said liquid including drive means having motor means mounted within said internal handle chamber for displaceably oscillating said bristles, rotating said bristles, and delivering said liquid external said head housing.

2. The toothbrush system as recited in claim 1 including a liquid container mounted within said internal handle chamber for dispensing said liquid responsive to actuation of said motor means.

3. The toothbrush system as recited in claim 2 where said liquid container is a flexible bellows, said means for delivering said liquid including a longitudinally directed head flow passageway formed in said head member in fluid communication with said flexible bellows.

4. The toothbrush system as recited in claim 3 where said means for delivering said liquid includes means for pulsating said liquid passing through said head member responsive to actuation of said drive means.

5. The toothbrush system as recited in claim 4 where said means for pulsating said liquid includes;
   (a) a first liquid conduit in fluid communication with said liquid container at a first end thereof;
   (b) a second liquid conduit in fluid communication with said head flow passageway;
   (c) a one-way valve member mounted on a second end of said first liquid conduit; and,
   (d) means for actuating said one-way valve for providing liquid flow from said first liquid conduit to said second liquid conduit responsive to actuation of said drive means.

6. The toothbrush system as recited in claim 5 where said means for actuating said one-way valve includes:
   (a) a piston chamber in fluid communication with said second liquid conduit and said one-way valve;
   (b) a linearly and reversibly displaceable piston member coupled to said drive means for creating a pressure differential between said piston chamber and said first liquid conduit for providing liquid flow from said first liquid conduit into said second liquid conduit.

7. The toothbrush system as recited in claim 6 wherein said means for delivering said liquid includes means for converting a rotational displacement of said drive means to a linear and reversible displacement of said piston member.

8. The toothbrush system as recited in claim 7 where said means for converting said rotational displacement of said drive means to said linear and reversible displacement of said piston member includes:
   (a) a longitudinally directed fork member having opposing fork member sidewalls defining a longitudinally directed fork slot;
   (b) a fork pin member slidable within said fork slot; and,
   (c) means for displacing said fork pin member responsive to actuation of said drive means.

9. The toothbrush system as recited in claim 8 where said means for displacing said fork pin member includes:
   (a) a first bevel gear mounted on a longitudinally extending shaft of said motor;
   (b) a second bevel gear in mating engagement with said first bevel gear for rotation of said second bevel gear about a second bevel gear axis normal to said longitudinal direction, said fork pin member mounted to said second bevel gear and extending in a direction substantially parallel to said second bevel gear axis.

10. The toothbrush system as recited in claim 9 where said piston member is mounted to one of said opposing fork member sidewalls and extending transverse thereto for linear reversible displacement into said piston chamber responsive to a displacement of said fork pin member.

11. The toothbrush system as recited in claim 8 where said drive means for displaceably oscillating said bristles includes:
    (a) a longitudinally directed head shaft member coupled to said bristles and said fork member;
    (b) means for converting said displacement of said fork member to an oscillating rotative displacement of said longitudinally directed head shaft member about said central axis.

12. The toothbrush system as recited in claim 11 where said means for converting said displacement of said fork member includes a ball joint member for coupling of said fork member and said head shaft.

13. The toothbrush system as recited in claim 11 where said means for rotating bristles about an axis substantially normal to said longitudinal direction includes:
    (a) a bristle head member having bristles extending from a first end thereof;
    (b) a bristle pinion gear mounted on a second end of said bristle head member, said bristle head member being displaceable within a slot formed through said head housing; and, (c) a stationary head rack gear for mating engagement with said bristle pinion gear, said head rack gear being rigidly coupled to said head housing.

14. The toothbrush system as recited in claim 13 including bristle head member bearing means providing for rotation of said bristle head member responsive to said displaceable oscillation of said bristles.

15. The toothbrush system as recited in claim 14 wherein said means for delivering said liquid includes a longitudinally directed head shaft conduit extending in said longitudinal direction and coupled in fluid communication to said second liquid conduit.

16. The toothbrush system as recited in claim 15 where said head shaft conduit is in fluid communication with a plurality of branch conduits passing through said bristle head member for passage of said liquid therethrough.

17. The toothbrush system as recited in claim 16 where said bristle head member is rotatably displaceable with respect to a respective branch conduit.

18. The toothbrush system as recited in claim 2 including:
    (a) an external reservoir for storing said liquid;
    (b) means for filling said liquid container responsive to a coupling of said toothbrush handle member to said reservoir.

* * * * *